United States Patent [19]

Vanlautem et al.

[11] 4,310,684
[45] Jan. 12, 1982

[54] PROCESS FOR SEPARATING POLY-β-HYDROXYBUTYRATES FROM A BIOMASS

[75] Inventors: Noël Vanlautem, Wavre; Jacques Gilain, Brussels, both of Belgium

[73] Assignee: Solvay & Cie., Brussels, Belgium

[21] Appl. No.: 109,537

[22] Filed: Jan. 4, 1980

[30] Foreign Application Priority Data

Jan. 22, 1979 [FR] France .................... 79 01862

[51] Int. Cl.$^3$ .................... C07C 69/675; C07C 67/56
[52] U.S. Cl. .................................................. 560/185
[58] Field of Search .................... 560/185; 435/146

[56] References Cited

U.S. PATENT DOCUMENTS 3,036,959  5/1962  Baptist .............................. 560/185
3,044,942  7/1962  Baptist .............................. 560/185

FOREIGN PATENT DOCUMENTS 7700840  1/1977  France .

OTHER PUBLICATIONS

*Chemical Abstracts*, vol. 74 (1971) #54,281p.
*Chemical Abstracts*, vol. 85 (1976) #178,134q.
Schlegel, H. G. et al. *Angewandte Chemie*, vol. 74 (1962) pp. 342-347.

*Primary Examiner*—Natalie Trousof
*Assistant Examiner*—L. Hendriksen
*Attorney, Agent, or Firm*—Spencer & Kaye

[57] ABSTRACT

A process for separating poly-β-hydroxybutyrates from a biomass by extraction using at least one liquid halogenated solvent selected from the group consisting of chloroethanes and chloropropanes.

6 Claims, No Drawings

PROCESS FOR SEPARATING POLY-β-HYDROXYBUTYRATES FROM A BIOMASS

BACKGROUND OF THE INVENTION

The present invention relates to a process for separating poly-β-hydroxybutyrates from a biomass by extraction using liquid halogenated solvents.

Numerous micro-organisms are capable of synthesising poly-β-hydroxybutyrates, the main function of which, in these micro-organisms, seems to be the storage of energy in the form of carbonaceous material. These poly-β-hydroxybutyrates constitute a valuable raw material from the industrial point of view. Various techniques have already been envisaged for separating them from biomasses. Thus, it has already been proposed to extract them from the biomass using liquid halogenated solvents of low boiling point, such as chloroform and methylene chloride. In these known processes, the extraction is generally carried out at the normal boiling point of the solvent or at a lower temperature. When carried out in this way, the extraction requires very long treatment times and is accompanied by depolymerisation of the poly-β-hydroxybutyrates, even though a low temperature is used.

In order to reduce the extraction times and increase the yields, it has been proposed to employ solvents, such as the cyclic carbonate of ethane-1,2-diol (ethylene carbonate) or the cyclic carbonate of propane-1,2-diol (propylene carbonate), at higher temperatures. In fact, these processes make it possible to achieve the aims, but they cause significant depolymerisation of the poly-β-hydroxybutyrates.

SUMMARY OF THE INVENTION

The object of the present invention is to provide a process which no longer exhibits any of the disadvantages of the known processes.

For this purpose, the present invention relates to a process for separating poly-β-hydroxybutyrates from a biomass by extraction using liquid halogenated solvents, in accordance with which process liquid halogenated solvents chosen from amongst chloroethanes and chloropropanes are used.

DETAILED DESCRIPTION OF THE INVENTION

Chloroethanes and chloropropanes are understood as denoting all the compounds derived from ethane or propane in which one or more hydrogen atoms has or have been substituted by a chlorine atom, and also the chloroethanes and the chloropropanes in which some hydrogen atoms have also been substituted by halogen atoms such as iodine and bromine and, preferably, fluorine. However, it is preferred to use chloroethanes and chloropropanes which are unsubstituted and which only contain chlorine, carbon and hydrogen atoms in the molecule.

Although the liquid medium used for the extraction according to the invention consists essentially of chloroethanes and chloropropanes, it can contain small amounts of other liquids. However, it preferably consists of chloroethanes and chloropropanes in a proportion of at least 90% by weight and more particularly at least 99% by weight.

The solvents used according to the invention can be used by themselves or in combination. The simplest procedure consists in employing only one solvent, which may be in the impure form, commonly referred to as being "of technical grade". Preferably, the solvents chosen have a boiling point of between 65° C. and 170° C., measured at atmospheric pressure.

The solvents which are very particularly preferred are the unsubstituted chloroethanes and chloropropanes in which the carbon atoms carrying at least one chlorine atom are also substituted by at least one hydrogen atom. In this category, the solvents which give the best results are 1,2-dichloroethane, 1,1,2-trichloroethane, 1,1,2,2-tetrachloroethane and 1,2,3-trichloropropane. The best results have been obtained with 1,2-dichloroethane and 1,1,2-trichloroethane.

The biomasses which can be treated according to the invention can be obtained from micro-organisms of various origins and, in particular, from bacteria, as described in Angew. Chemie 1962, 74, No. 10, pages 342–346. The micro-organisms are generally selected on the basis of the relative amount of poly-β-hydroxybutyrates present in the micro-organism, and also in accordance with the rate of growth of the micro-organism and of the rate at which it synthesises the poly-β-hydroxybutyrates.

Whether the micro-organisms have been cultivated artificially or not, they can be treated directly with the extraction solvent in their culture medium. However, a preferred procedure consists in starting from micro-organisms which have been separated from their culture medium prior to extraction. This separation can be carried out by any means known for this purpose. An elegant procedure consists in centrifuging the culture medium so that the micro-organisms can easily be separated from the medium, and in subsequently lyophilising the isolated micro-organisms so as to obtain a biomass which can easily be treated with the extraction solvent.

The ratio of the amount of biomass employed to the amount of extraction solvent used is not in itself critical. The process is generally carried out with weight ratios of between 1:1 and 1:100. Normally, ratios of between 1:2 and 1:50 are employed and, in fact, the process is preferably carried out with ratios of between 1:5 and 1:10. The choice of this ratio is influenced by various parameters such as the nature of the biomass to be treated, the temperature, the number of extractions and the yield which it is desired to achieve by extraction. Moreover, the smaller the amount of biomass in the extraction medium, the easier is the removal of the cell residues.

The temperature at which the extraction is carried out is chosen in accordance with the nature of the chloroethanes and chloropropanes used. Temperatures which are generally very suitable are between 50° C. and the boiling point, measured under atmospheric pressure, of the solvent. It has been found that the optimum operating temperatures are usually below 130° C. They are preferably between 60° and 90° C. In the case of 1,2-dichloroethane, good results have been obtained at between 60° and 80° C.

The pressure at which the extraction is carried out is not critical and is generally between 0.1 and 10 kg/cm$^2$.

The extraction operation can be carried out in any equipment designed for this purpose. The operation can be carried out continuously or discontinuously, the biomasses and the extraction solvents circulating in the same direction or in opposite directions.

After the extraction operation, the compounds which are insoluble in the medium, such as the cell membranes from the biomass which has been subjected to extraction, can be removed from the solvent. This can be effected using any known means. This operation is normally carried out by means of one or more filtrations.

The extracted poly-β-hydroxybutyrates can be separated from the extraction medium by any method known for this purpose. Thus, they can be separated off by evaporating off the solvent or also by simply adding a precipitant. Compounds which are non-solvents for the poly-β-hydroxybutyrates, such as petroleum ether, unsubstituted aliphatic hydrocarbons, aromatic solvents, including benzene, or also aliphatic alcohols, may be mentioned as precipitants which can be used. Preferred precipitants are aliphatic alcohols and more particularly, for economic reasons, methanol and ethanol.

The poly-β-hydroxybutyrates separated off according to the invention can subsequently be purified by washing once or several times with non-solvents, such as those mentioned above, and dried, and they are then in the form of a white polymeric mass. The recovery and purification operations are normally carried out at ambient temperature.

Poly-β-hydroxybutyrates are polymers having a large number of applications, especially in surgery where they can be used in the form of threads because they can easily be sterilised. Moreover, these polymers can be shaped, by the various known moulding techniques, in order to produce prostheses. They can also be spun or extruded in accordance with the usual methods.

The following examples serve to illustrate the invention.

EXAMPLE 1 (COMPARISON)

100 ml of chloroform are introduced into a 250 ml round-bottomed flask equipped with a stirrer and a water-cooled condenser and are heated to 60° C. 16.0 g of a lyophilised dried biomass, which consists of bacteria of the ALCALIGENES EUTROPHUS strain, has been crumbled in a mortar before use and has a surface water content of 23.2 g/kg, are then introduced. After 1 hour, the solution is removed and filtered hot, under pressure, on a fabric cloth in order to remove the solid residues of the biomass. The polymer is precipitated by adding excess ethanol, at ambient temperature, to the resulting solution. The precipitate is filtered off in vacuo on a filter fitted with a glass frit, and is washed with ethanol. The polymer is then dried in vacuo to constant weight. The yield of the extraction is given by the weight of the extracted product relative to the weight of biomass employed, and the weight-average molecular weight of the polymer is calculated by measuring the intrinsic viscosity of a chloroform solution in accordance with the formula $(\eta) = 1.9 \cdot 10^{-2} M_w^{0.74}$  ($\eta$ expressed in ml/g)

recommended in the article published in Makromol. Chem., Volume 176, 1975, page 2,662. Some values obtained are summarised in Table 1 below.

EXAMPLES 2 AND 3 (COMPARISON)

Example 1 is repeated, but the chloroform is replaced respectively by carbon tetrachloride (Example 2) and trichloroethylene (Example 3). The results obtained are summarised in Table 1.

EXAMPLES 4, 5 AND 6

The process is again carried out under identical conditions to those of Example 1, but the extraction operation is carried out with 1,2-dichloroethane (Example 4), 1,1,2-trichloroethane (Example 5) and 1,1,2,2-tetrachloroethane (Example 6). The results obtained are also recorded in Table 1 below.

EXAMPLE 7 (COMPARISON)

Example 1 is repeated using chloroform as the extraction solvent, but the extraction is carried out for a period of 3 hours. The results obtained are recorded in Table 1 below.

TABLE 1

| Experiment No. | 1 | 2 | 3 | 4 | 5 | 6 | 7 |
|---|---|---|---|---|---|---|---|
| Yield % | 36.6 | 0 | 0 | 66.2 | 72.0 | 60.7 | 48.8 |
| Molecular weight × $10^{-3}$ | 887 | — | — | 902 | 920 | 905 | 576 |

It can therefore be concluded from the results summarised in Table 1 that the yields observed when effecting extraction according to the invention are substantially higher than in the case where other halogenated solvents are used under the same operating conditions. These yields are even higher than those obtained after an extraction period of three times the length, using a typical halogenated solvent of the prior art.

Moreover, it can be seen that, in Examples 4, 5 and 6, the molecular weights of the polymers separated off according to the invention are substantially higher than those obtained with chloroform at the same temperature.

EXAMPLE 8 (COMPARISON)

The procedure of Example 1 is followed, but the extraction is carried out at 120° C. instead of 60° C. and propylene carbonate is used instead of chloroform. The yield observed and the molecular weight of the extracted polymer are recorded in Table 2 below.

EXAMPLES 9 AND 10

The procedure of Example 8 is followed, but the propylene carbonate is replaced by 1,1,2,2-tetrachloroethane (Example 9) and by 1,2,3-trichloropropane (Example 10). The results are summarised in Table 2.

TABLE 2

| Experiment No. | 8 | 9 | 10 |
|---|---|---|---|
| Yield % | 67.6 | 65.5 | 63.7 |
| Molecular weight × $10^{-3}$ | 400 | 574 | 693 |

It can therefore be deduced from these results that the invention makes it possible to obtain, at a given temperature, extraction yields which are of the same order of magnitude as those obtained with propylene carbonate, without at the same time causing such a high degree of depolymerisation of the extracted polymer.

Moreover, it can be deduced, by comparing the results of Tables 1 and 2, that the invention makes it possible to obtain extraction yields, at a temperature of 60° C., which are better than or at least equal to the yields of the known processes at 120° C., without causing such a high degree of depolymerisation.

What is claimed is:

1. Process for separating poly-β-hydroxybutyrates from a biomass by extraction using liquid halogenated solvents, comprising performing the extraction with at least one liquid halogenated solvet selected from the group consisting of 1,2-dichloroethane, 1,1,2-trichloroethane, and 1,1,2,2-tetrachloroethane.

2. Process according to claim 1, wherein the extraction is carried out at a temperature between 60° and 90° C.

3. Process according to claim 1 comprising initially separating said biomass from the culture medium.

4. Process according to claim 2, wherein the ratio of biomass to extraction solvent is between 1:1 and 1:100.

5. Process according to claim 2, wherein the ratio of biomass to extraction solvent is between 1:5 and 1:10.

6. Process according to claim 2 comprising performing the extraction at a pressure between 0.1 and 10 kg/cm$^2$.

* * * * *